United States Patent [19]

Goedecke et al.

[11] 4,245,090
[45] * Jan. 13, 1981

[54] PROCESS FOR THE RECOVERY OF CYANURIC CHLORIDE

[75] Inventors: Ralf Goedecke, Rodenbach; Martin Liebert, Steinbach; Wolfgang Nischk, Wesseling, all of Fed. Rep. of Germany; Wolfgang Plötz, Mobile, Ala.; Kurt Puschner, Frankfurt, Fed. Rep. of Germany

[73] Assignee: Deutsche Gold- und Silber-Scheideanstalt vormals Roessler, Frankfurt, Fed. Rep. of Germany

[*] Notice: The portion of the term of this patent subsequent to Jan. 13, 1998, has been disclaimed.

[21] Appl. No.: 78,831

[22] Filed: Sep. 25, 1979

[30] Foreign Application Priority Data

Oct. 5, 1978 [DE] Fed. Rep. of Germany ....... 2843382

[51] Int. Cl.$^3$ ............................................. C07D 251/28
[52] U.S. Cl. .................................................... 544/191
[58] Field of Search ......................................... 544/191

[56] References Cited

U.S. PATENT DOCUMENTS

| | | | |
|---|---|---|---|
| 3,256,070 | 6/1966 | Trickey .................................. | 23/294 |
| 3,338,898 | 8/1967 | Foulletier ............................. | 544/191 |
| 3,409,619 | 11/1968 | Kosel .................................... | 260/248 |
| 3,539,565 | 11/1970 | Evers .................................... | 260/248 |
| 3,761,472 | 9/1973 | Riethmann et al. ................. | 544/191 |
| 3,925,377 | 12/1975 | Geiger et al. ........................ | 544/191 |
| 4,038,276 | 7/1977 | Geiger et al. ........................ | 544/191 |

FOREIGN PATENT DOCUMENTS 1266308   4/1968   Fed. Rep. of Germany .

OTHER PUBLICATIONS

Ullmann, Enzyklopadie der technischen Chemie, 3rd Edition, (1954) vol. 5, pp. 624 and 625.

*Primary Examiner*—John M. Ford
*Attorney, Agent, or Firm*—Cushman, Darby & Cushman

[57] ABSTRACT

There is provided a process for the recovery of cyanuric chloride in solid or liquid form from the reaction mixture which results from the trimerization of cyanogen chloride wherein to recover the cyanuric chloride at will in liquid or solid form the gaseous reaction mixture is introduced into an apparatus combination consisting essentially of a stripping column and a condenser connected at the outlet side, preferably a head condenser, preferably above the stripping column, and in which the sump of the stripping column is held to the boiling temperature of the cyanuric chloride whereupon the cyanuric chloride contained in the gaseous reaction mixture depending on the regulation of the temperature at the outlet of the condenser in the range of 146° to 190° C. is partially condensed, after which to recover the liquid cyanuric chloride in liquid form it is removed as such at the lower end of the stripping column and is either directly or, in a given case, after an intermediate storage led to a spray tower and is sprayed whereupon the solid, fine-grained cyanuric chloride is withdrawn at the bottom of the spray tower while the residual gas leaving the condenser and still containing cyanuric chloride, which amount of cyanuric chloride is controlled by the temperature at the outlet of the condenser, is led preferably to a separating chamber and the residual cyanuric chloride is recovered there by known process.

6 Claims, 1 Drawing Figure

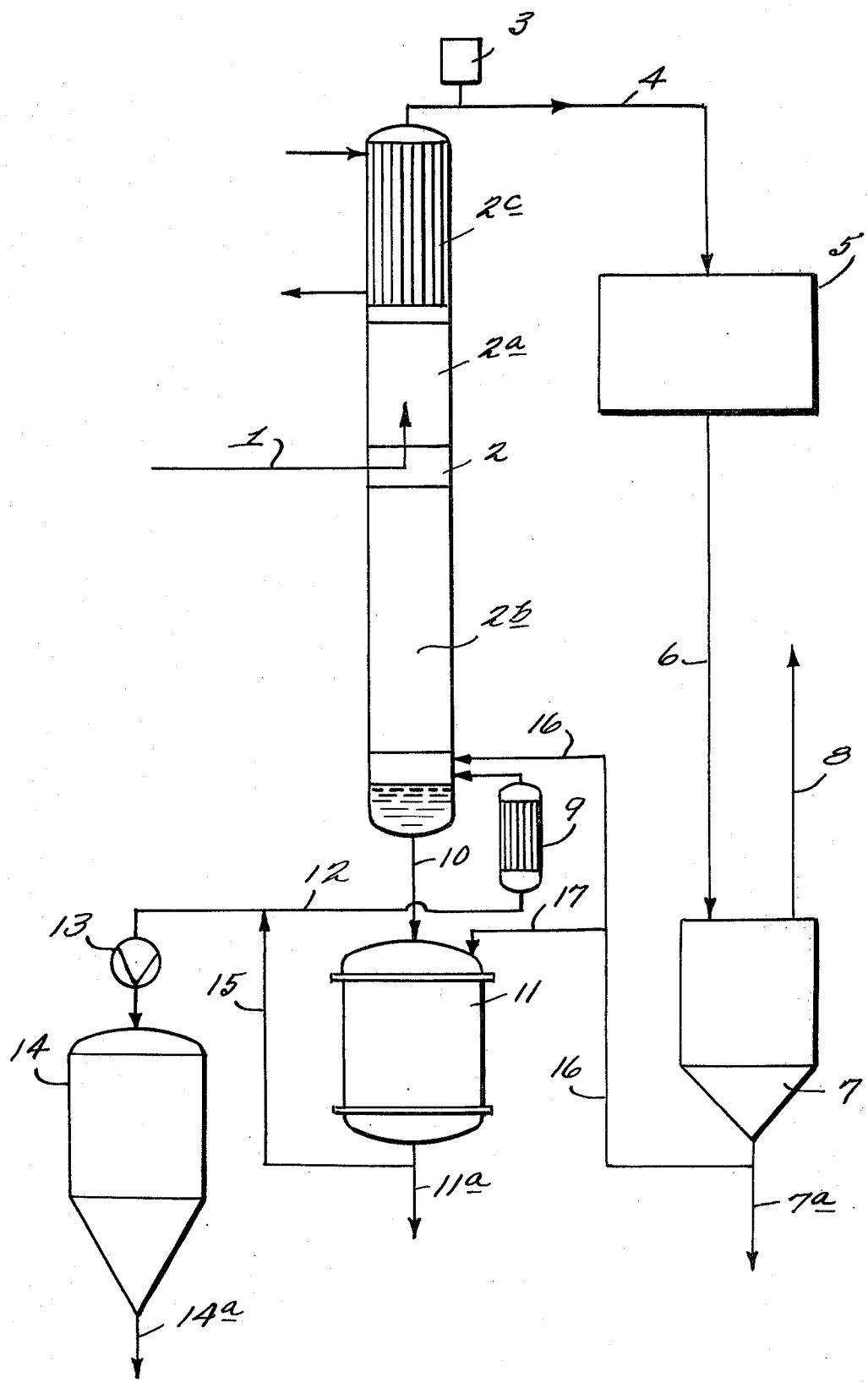

PROCESS FOR THE RECOVERY OF CYANURIC CHLORIDE

BACKGROUND OF THE INVENTION

Cyanuric chloride which is recovered by trimerization of cyanogen chloride with the help of catalyst, above all activated carbon, as is known is a very interesting intermediate product for various industrial sectors such as the production of dyestuffs and products for the textile industry, as well as for pharmaceuticals, products for agriculture as well as for the synthetic resin, rubber and explosives industries.

As is known after the trimerization cyanuric chloride is obtained in gaseous form together with unreacted cyanogen chloride and chlorine as well as byproducts.

For a long time, it was customary to convert this gaseous reaction mixture directly into solid cyanuric chloride, e.g., by conducting the gaseous mixture into a chamber cooled from the outside (see Ullmann, Enzyklopädie der technischen Chemie, 3rd Edition, 1954, Volume 5, pages 624–625 and 4th Edition, 1975, Volume 9, page 652).

It has also been passed into a ball mill cooled with water according to the process of Trickey U.S. Pat. No. 3,256,070.

Solid cyanuric chloride generally is obtained in powdery form and until now was predominantly further processed in this form.

A disadvantage of the solid cyanuric chloride, however, is that it is frequently not simple to handle.

In filling containers and storing as well as in further processing it precautions were necessary.

Besides there are certain industrial difficulties connected with the deposition in solid form since the cyanuric chloride deposits partially in the form of coarse crystals on the walls and installations in the deposition receiver and delivery aggregate.

These coarse crystals must be knocked off mechanically and then led to a clear impairment of the quality of the final product.

In order to avoid the deposition of coarse crystals inert cooling liquids have been sprayed via nozzles in the deposition of the solid cyanuric chloride, see German Pat. No. 1,266,308 and related Kosel U.S. Pat. No. 3,409,619.

However, in connection therewith there occurs encrustations on the nozzles and cloggings.

For reasons of work hygiene and environmental protection as well as with the coming into use of ever increasing automatic processes it was necessary to recover cyanuric chloride in a form better to handle and to process.

Cyanuric chloride in liquid or dissolved form offers a way of doing this. The presence of cyanuric chloride in dissolved form, however, requires a fairly large expense for the manufacture and recovery of the solvent.

Besides there occur waste gas problems which additionally complicate the process, see Evers U.S. Pat. No. 3,539,565.

The solvent used in each case also must be adjusted according to the later intended area of use and the solubility of cyanuric chloride in the individual solvents is quite varied.

Furthermore there are known processes in which gaseous cyanuric chloride is liquefied with the help of a liquid assistant. These liquid assistants, as e.g., phosphorus oxychloride should prevent the cyanuric chloride from passing out of the fractionating column.

However, the use of such a liquid assistant requires an expensive apparatus for working up and recycling the liquid assistant employed, as well as for purification of the waste gas.

Furthermore it has been shown that accidental break through of the liquid assistant into the liquid cyanuric chloride phase leads to considerable loss of quality.

Besides because of the increasing importance of the liquid cyanuric chloride and the high market share of powdery cyanuric chloride it would be desirable if a process existed according to which both phases could be recovered in the same apparatus and in a simple manner.

Thus the object of the invention is to develop a process for the production of cyanuric chloride in which the cyanuric chloride can be recovered substantially at will in liquid or solid form.

SUMMARY OF THE INVENTION

It has now been found that cyanuric chloride can be recovered in solid or liquid form from the gaseous reaction mixture resulting from the trimerization of cyanogen chloride if to recover the cyanuric chloride at will in liquid or solid form the gaseous reaction mixture is introduced into an apparatus combination consisting essentially of a stripping column and a condenser connected at the outlet side, preferably a head condenser, preferably above the stripping column, and in which the sump of the stripping column is held to the boiling temperature of the cyanuric chloride whereupon the cyanuric chloride contained in the gaseous reaction mixture depending on the regulation of the temperature at the outlet of the condenser in the range of 146° to 190° C. is partially condensed, after which to recover the liquid cyanuric chloride in liquid form it is removed as such at the lower end of the stripping column and is either directly or, in a given case, after an intermediate storage led to a spray tower and is sprayed whereupon the solid, fine-grained cyanuric chloride is withdrawn at the bottom of the spray tower while the residual gas leaving the condenser and still containing cyanuric chloride, which amount of cyanuric chloride is controlled by the temperature at the outlet of the condenser, is led preferably to a separating chamber and the residual cyanuric chloride is recovered there by known process.

The constituent amounts "liquid-solid" of cyanuric chloride which are obtained in the process of the invention are regulated through the choice of gas temperature at the outlet of the condenser.

Also if the cyanuric chloride recovered in powdery form, e.g., through sublimation, should be ultimately is intended to be obtained in liquid form then the solid product produced in the separating chamber can either be melted or, e.g., lead to the stripping column. However, it is also possible to feed the solid product directly to the molten product which leaves the stripping column whereby it itself likewise is melted.

However, the molten product can also be conducted to the spray tower, namely either together with the previously recovered liquid portion, or, if necessary, alone.

Thus in the extreme case, if it is desired, the entire amount of cyanuric chloride obtained in the gaseous reaction mixture can be recovered in liquid form.

However, it is also possible according to the process of the invention to recover the cyanuric chloride as 100% solid, namely in the case where even the liquid portion which also can contain the portion resulting from the separation chamber and again melted is completely sprayed.

The sprayed product is superior to the powdery product obtained by previously known processes in regard to pourability and usefulness in reaction.

Thus it is possible without further ado according to the invention, as desired, to obtain a part of the cyanuric chloride in liquid form and the rest in solid form or to obtain the entire cyanuric chloride in either liquid or solid form.

Such a flexible process which could be carried out in one and the same plant was not known previously.

However, it has also surprisingly been shown that even the powdery portion of the cyanuric chloride which accumulates in the separation chamber is superior to the powdery cyanuric chloride which is recovered according to known processes since, because of the high portion of residual gas which leaves the condenser, it is obtained in finely divided form.

The amount of residual gas which leaves the condenser, as is known, is dependent on the degree of trimerization of the cyanogen chloride in the gaseous reaction mixture, i.e., on the nature of the catalyst and accordingly the condition in the trimerization portion. This residual gas is preferably, as previously set forth, processed for the recovery of the gaseous cyanuric chloride present therein, e.g., in a separation chamber, if it does not leave the system as such and is not destroyed in some form.

Conventional distillation columns serve as the stripping or distillation column.

There are employed as condensers known heat exchangers, preferably heat exchangers with tube bundles. These condensers can either be connected to the discharge end of the distillation (stripping) column or, as previously stated, preferably be arranged as head condensers.

The elimination of heat preferably occurs through known heat transfer media.

Of course, it is possible to directly supply the gaseous reaction mixture to the stripping column, but it has proven favorable energywise to introduce the reaction gas above the stripping column into the apparatus combination. Especially favorable is the installation of an intermediate element in the apparatus combination, namely between the gas inlet above the stripping column and the condenser. In this intermediate element the condensing gaseous reaction mixture experiences an intermediate cooling before it enters the condenser.

As spray towers and separation chambers, there can be used customary apparatus with air or liquid cooling.

As the spraying organ of the spray tower there serve all apparatus suited for this purpose such as deflectors, unitary and binary nozzles of various construction which are based on various types of atomizing principles.

The advance in the art of the process of the invention is first, as already said, in the flexibility of the process in which at will liquid and solid portions of cyanuric chloride can be recovered from the gaseous reaction mixture in conjunction with the trimerization of cyanogen chloride.

Additionally, the industrially easy to carry out process only requires a few process steps since the process is managed without additional chemical substances.

Furthermore, the end product is distinguished by great purity, and what is of concern to the solid product, by an especially fine grain and even improved pourability.

Besides the liquid cyanuric chloride is preferably obtained free from chlorine and cyanogen chloride, e.g., by driving out the dissolved gases from the liquefied cyanuric chloride.

Additionally, the process operates in a manner favorable to the environment since the toxic components contained in the residual gases as, e.g., chlorine and cyanogen chloride can be removed by conventional washing processes and in a given case again returned into the production of cyanogen chloride.

BRIEF DESCRIPTION OF THE DRAWING

The single FIGURE of the drawings illustrates schematically an apparatus for carrying out the process of the invention.

Referring more specifically to the drawing, the overheated gaseous reaction mixture which is composed of cyanuric chloride vapor and the residual gas of chlorine, cyanogen chloride and inert gases and which leaves the trimerization reactor (not shown) goes via conduit 1 into the apparatus combination 2.

The apparatus combination consists of the distillation or stripping column 2b and the head or top condenser 2c. In a given case by inserting the intermediate element 2a the cooling of the vaporous mixture takes place to saturated vapor temperature whereby a portion of the cyanuric choride condensate running out of the condenser is again vaporized.

Without intermediate element 2a the vapor mixture is introduced directly below the condenser 2c and is cooled there.

A portion of cyanuric chloride vapor mixture entering apparatus combination 2 is liquefied in condenser 2c, the remaining portion together with the non-condensed gases is totally led via line 4 to the separation chamber 5 for depositing solids.

The ratio of condensed to gaseous remaining cyanuric chloride is regulated with the help of temperature measuring and control place 3 at the outlet of condenser 2c.

The solid material obtained in the separation chamber 5 passes via line 6 into the storage container 7 and can be withdrawn via line 7a.

The residual gas removed from the storage container 7 is drawn off by suction via the line 8 and sent to a waste gas purification step (not shown).

Should the cyanuric chloride melt likewise be converted into solid form then it can be led both directly via line 12 and from the storage container 11 and line 15 by means of the pump 13 to the spray tower 14 and there sprayed and withdrawn via line 14a as a sprayed solid product.

In the case that the solid cyanuric chloride produced in the separation chamber 5 should be present in liquid form, the solid cyanuric chloride is led either via line 16 to the sump of the stripping column 2b or via line 17 to the storage container 11.

All parts of the apparatus and lines which contain or carry the cyanuric chloride melt must be heated to temperatures above the melting point of cyanuric chloride.

In the stripping portion of the stripping column 2b the residual gases dissolved in the liquefied cyanuric chloride, above all chlorine and cyanogen chloride, are removed.

For this a sump temperature is necessary which is greater than or equal to the boiling temperature of the liquid cyanuric chloride at the corresponding column pressure and it is maintained with the help of the vaporizer 9.

The thus produced cyanuric chloride melt purified from residual gases is supplied through the line 10 to the storage container 11 from which it can be withdrawn via line 11a.

Unless otherwise indicated all parts and percentages are by weight.

The process can comprise, consist essentially of or consist of the steps set forth and the materials employed can comprise, consist essentially of or consist of those set forth.

DESCRIPTION OF THE PREFERRED EMBODIMENTS

EXAMPLE 1

A mixture of 981 kg of cyanuric chloride vapor and 70 kg of residual gas ($N_2$, $Cl_2$, ClCN, $CO_2$) were supplied hourly to the stripping column 2b. The pressure of the mixture was 794 Torr and its temperature 225° C.

After the cooling to the saturated vapor temperature of 191° C. in the intermediate element 2a the mixture was cooled to 150° C. in the condenser 2c. To separate the dissolved residual gases in the liquefied cyanuric chloride there was led a cyanuric chloride vapor stream of 196 kg/h from the sump counter to the liquid stream running downwardly in the column.

In the sump of the column there were obtained 891 kg/h of practically pure cyanuric chloride melt. This melt was sprayed in a spray tower with a binary nozzle. Thereby there was obtained the following particle size distribution.

<50μ: 93.7 weight %
50–71μ: 4.1 weight %
72–100μ: 2.0 weight %
>100μ: 0.2 weight %

The residual gas saturated with cyanuric chloride and having a temperature of 150° C. left the head condenser 2c and was supplied via the ine 4 to the desublimation chamber 5.

After the separation of the particle shaped cyanuric chloride composition stream of 90 kg/h from the mixture of gaseous cyanuric chloride and residual gas the finely divided cyanuric chloride particles and the residual gas were conveyed via line 6 into the silo 7.

The residual gas composition stream with a cyanuric chloride portion of less than 0.1 weight % was conveyed out of the silo 7 to the waste gas purification via the line 8.

The residual gas had the following composition.
ClCN: 14 weight %
$Cl_2$: 54 weight %
$CO_2$: 27 weight %
$N_2$: 5 weight %

The particle size distribution of the cyanuric chloride which accumulated in the desublimation chamber corresponded to the following values.
<50μ: 30 weight %
50–71μ: 52 weight %
72–100μ: 14.5 weight %
101–160μ: 3.2 weight %
>160μ: 0.3 weight %

EXAMPLE 2

A mixture of 981 kg of cyanuric chloride vapor and 70 kg of residual gas ($N_2$, $Cl_2$, ClCN, $CO_2$) were supplied hourly to the stripping column 2b. The pressure of the mixture was 794 Torr and its temperature was 225° C.

After the cooling to the saturation vapor temperature of 191° C. in the intermediate element 2a the mixture was cooled to 163° C. in the condenser 2c. To separate the dissolved residual gases in the liquefied cyanuric chloride there was led a cyanuric chloride vapor stream of 181 kg/h from the sump counter to the liquid stream running downwardly in the column.

In the sump of the column there were obtained 821 kg/h of practically pure cyanuric chloride melt. The residual gas saturated with cyanuric chloride and having a temperature of 163° C. left the head condenser 2c and was supplied via line 4 to the desublimation chamber 5.

After the separation of the particle shaped cyanuric chloride composition stream of 160 kg/h from the mixture of gaseous cyanuric chloride and residual gas the finely divided cyanuric chloride particles and residual gas were conveyed via line 6 into the silo 7.*

*The residual gas composition stream with a cyanuric chloride portion of less than 0.1 weight-% was supplied from the silo 7 to the waste gas purification via line 8.

The residual gas composition corresponded to that of Example 1.

The final product had a particle size distribution of:
<50μ: 29.0 weight %
50–71μ: 47.0 weight %
72–100μ: 17.9 weight %
101–160μ: 4.8 weight %
>160μ: 1.3 weight %

EXAMPLE 3

A mixture of 1018 kg of cyanuric chloride vapor and 73 kg of residual gas ($N_2$, $Cl_2$, ClCN, $CO_2$) were supplied hourly to the stripping column 2b. The pressure of the mixture was 794 Torr and its temperature was 225° C.

After the cooling to the saturation vapor temperature of 191° C. in the intermediate element 2a the mixture was cooled to 180° C. in the condenser 2c. To separate the dissolved residual gases in the liquefied cyanuric chloride there was led a cyanuric chloride vapor stream of 118 kg/h from the sump counter to the liquid stream running downwardly in the column.

In the sump of the column there was obtained 534 kg/h of practically pure cyanuric chloride melt. The residual gas saturated with cyanuric chloride and having a temperature of 180° C. left the head conderser 2c and was supplied via line 4 to the desublimation chamber 5.

After the separation of the particle shaped cyanuric chloride composition stream of 483 kg/h from the mixture of gaseous cyanuric chloride and residual gas the finely divided cyanuric chloride particles and the residual gas were conveyed via line 6 into the silo 7.

The residual gas composition stream with a cyanuric chloride portion of less than 0.1 weight % was supplied from the silo 7 to the waste gas purification via line 8.*

*The residual gas composition corresponded to that of example 1.

The final product had a particle size distribution of:
<50μ: 33.0 weight %

50–71μ: 51.3 weight %
72–100μ: 13.1 weight %
101–160μ: 2.4 weight %
>160μ: 0.2 weight %

EXAMPLE 4

A mixture of 981 kg of cyanuric chloride vapor and 49 kg of residual gas (N$_2$, Cl$_2$, ClCN, CO$_2$) were supplied hourly to the stripping column 2b. The pressure of the mixture was 794 Torr and its temperature was 225° C.

After the cooling to the saturation vapor temperature of 191° C. in the intermediate element 2a the mixture was cooled to 150° C. in the condenser 2c. To separate the dissolved residual gases in the liquefied cyanuric chloride there was led a cyanuric chloride vapor stream of 193 kg/h from the sump counter to the liquid stream running downwardly in the column.

In the sump of the column there was obtained 877 kg/h of practically pure cyanuric chloride melt. The residual gas saturated with cyanuric chloride and having a temperature of 150° C. left the head condenser 2c and was supplied via line 4 to the desublimation chamber 5.

After the separation of the particle shaped cyanuric chloride composition stream of 104 kg/h from the mixture of gaseous cyanuric chloride and residual gas the finely divided cyanuric chloride particles and the residual gas were conveyed via line 6 into the silo 7.

The residual gas composition stream with a cyanuric chloride portion of less than 0.1 weight % was supplied from the silo 7 to the waste gas purification via line 8.

The residual gas was composed of the individual components as follows:
ClCN: 47 weight %
Cl$_2$: 22 weight %
CO$_2$: 29 weight %
N$_2$: 2 weight %

The final product had a particle size distribution of:
<50μ: 30.0 weight %
50–71μ: 48.7 weight %
72–100μ: 17.4 weight %
101–160μ: 3.4 weight %
>160μ: 0.5 weight %

The entire disclosure of German priority application No. P 28 43 382.1-44 is hereby incorporated by reference.

What is claimed is:

1. A process for the recovery of cyanuric chloride in solid or liquid form from the reaction mixture which results from the trimerization of cyanogen chloride wherein in order to recover the cyanuric chloride at will in liquid form, in solid form or in both liquid and solid form the process comprises the steps of introducing the gaseous reaction mixture into an apparatus consisting essentially of a stripping column and a condenser connected at the outlet side thereof above the stripping column, holding the sump of the stripping column at the boiling temperature of the cyanuric chloride, regulating the temperature at the outlet of the condenser in the range of 146° to 190° C. to partially condense the cyanuric chloride, removing cyanuric chloride to be recovered in liquid form from the lower end of the stripping column, leading the removed liquid cyanuric chloride to a spray tower, spraying the removed liquid cyanuric chloride to form solid cyanuric chloride and withdrawing the solid sprayed cyanuric chloride from the spray tower, conveying gas leaving the condenser and still containing cyanuric chloride to a separating chamber and recovering the residual cyanuric chloride therefrom as a solid by desublimation, the amount of cyanuric chloride in the residual gas being controlled by the temperature at the outlet of the condenser.

2. The process of claim 1 wherein there is recovered only liquid cyanuric chloride by controlling the temperature at the outlet of the condenser.

3. The process of claim 1 wherein there is recovered only finely divided solid cyanuric chloride by controlling the temperature at the outlet of the condenser.

4. The process of claim 1 wherein there is recovered both liquid cyanuric chloride and solid, finely divided cyanuric chloride by controlling the temperature at the outlet of the condenser.

5. The process of claim 1 including the step of freeing the liquid cyanuric chloride condensed in the stripping column from dissolved chlorine and cyanogen chloride.

6. The process of claim 1 wherein said condenser is at the head of the column.

* * * * *